United States Patent
Patke

(10) Patent No.: US 6,596,084 B1
(45) Date of Patent: Jul. 22, 2003

(54) PYROLYTIC CARBON COATING APPARATUS HAVING FEED GAS ACTUATOR

(75) Inventor: Nandkishor G. Patke, Shoreview, MN (US)

(73) Assignee: MedicalCV, Inc., Inver Grove Heights, MN (US)

( * ) Notice: Subject to any disclaimer, the term of this patent is extended or adjusted under 35 U.S.C. 154(b) by 0 days.

(21) Appl. No.: 09/574,479

(22) Filed: May 19, 2000

Related U.S. Application Data

(60) Provisional application No. 60/135,000, filed on May 20, 1999.

(51) Int. Cl.[7] .................. C23C 16/00; H05H 1/02
(52) U.S. Cl. ............... 118/716; 118/715; 118/696; 118/695; 427/459; 427/461
(58) Field of Search ................... 118/715, 724, 118/696, 716; 427/459, 461

(56) References Cited

U.S. PATENT DOCUMENTS

| | | |
|---|---|---|
| 3,298,921 A | 1/1967 | Bokros et al. |
| 3,370,113 A | 2/1968 | Goeddel |
| 3,399,969 A | 9/1968 | Bokros et al. |
| 3,539,334 A | 11/1970 | Goeddel et al. |
| 3,547,676 A | 12/1970 | Bokros et al. |
| 3,625,745 A | 12/1971 | Wright et al. |
| 3,673,612 A | 7/1972 | Merrill et al. |
| 3,676,179 A | 7/1972 | Bokros |
| 3,677,795 A | 7/1972 | Bokros et al. |
| 3,677,800 A | 7/1972 | Wright |
| 3,685,059 A | 8/1972 | Bokros et al. |
| 3,707,006 A | 12/1972 | Bokros et al. |
| 3,764,469 A | 10/1973 | Bokros |
| 3,790,036 A * | 2/1974 | Miller .................. 406/128 |
| 3,877,080 A | 4/1975 | Olcott |
| 3,952,334 A | 4/1976 | Bokros et al. |
| 3,969,130 A | 7/1976 | Bokros |
| 3,977,896 A | 8/1976 | Bokros et al. |
| 4,038,703 A | 8/1977 | Bokros |
| 4,080,927 A | 3/1978 | Brown |
| 4,098,224 A | 7/1978 | Noren et al. |
| 4,116,160 A | 9/1978 | Langley et al. |
| 4,126,924 A | 11/1978 | Akins et al. |
| 4,178,639 A | 12/1979 | Bokros |
| 4,194,027 A | 3/1980 | Adams et al. |
| 4,221,182 A | 9/1980 | Brown |
| 4,529,573 A * | 7/1985 | Varady .................. 422/111 |
| 4,594,270 A | 6/1986 | Brooks |

(List continued on next page.)

FOREIGN PATENT DOCUMENTS

| | | | |
|---|---|---|---|
| EP | 0 055 406 B1 | 3/1985 | |
| WO | WO-00/71779 A1 * | 11/2000 | ........... C23C/16/00 |

OTHER PUBLICATIONS

Akins, R.J. and Bokros, J.C.; The Deposition of Pure and Alloyed Isotropic Carbons in Steady–State Fluidized Beds, *Carbon*, 1974, vol. 12, pp. 439–452.

*Primary Examiner*—Parviz Hassanzadeh
(74) *Attorney, Agent, or Firm*—Moore & Hansen

(57) ABSTRACT

A fluidized bed pyrolytic carbon coating apparatus (1) is provided for coating substrate surfaces with pyrolytic carbon. The preferred coating apparatus (1) includes a fluidized bed reactor (10) having a reactor chamber (22), a gas feed inlet (24), an exhaust gas outlet (26), a source (12) of process feed gas and a gas line (14) through which the process feed gas can pass from the source (12) of process feed gas to the gas feed inlet (24) and into the reactor chamber (22). The gas line (14) includes an actuator (20) having a timing circuit (37) which acts to vary a rate of flow of process feed gas through the gas line (14) into the reactor chamber (22) such that the rate of flow into the reactor chamber (22), cycles regularly and consistently over a period of time so as to create a pulsating gas flow and a pulsation effect upon the fluidized bed within the reactor chamber (22).

8 Claims, 3 Drawing Sheets

U.S. PATENT DOCUMENTS

| | | |
|---|---|---|
| 5,084,151 A | 1/1992 | Vallana et al. |
| 5,133,845 A | 7/1992 | Vallana et al. |
| 5,171,734 A | 12/1992 | Sanjurjo et al. |
| 5,262,104 A | 11/1993 | Schwartz |
| 5,284,676 A * | 2/1994 | Accuntius et al. ............. 427/8 |
| 5,305,554 A | 4/1994 | Emken et al. |
| 5,328,713 A | 7/1994 | Emken et al. |
| 5,328,720 A | 7/1994 | Emken et al. |
| 5,332,337 A | 7/1994 | Wilde et al. |
| 5,376,111 A | 12/1994 | Bokros et al. |
| 5,514,410 A * | 5/1996 | Ely et al. ................... 427/2.24 |
| 5,545,216 A | 8/1996 | Bokros et al. |
| 5,677,061 A * | 10/1997 | Ely et al. ..................... 428/408 |
| 5,990,250 A * | 11/1999 | Parrish et al. ................ 526/61 |
| 6,336,500 B2 * | 1/2002 | Hyppanen ................... 165/96 |

* cited by examiner

PYROLYTIC CARBON COATING APPARATUS HAVING FEED GAS ACTUATOR

CROSS-REFERENCE TO OTHER APPLICATIONS

The present application claims priority to U.S. Provisional Application Ser. No. 60/135,000 entitled PYROLYTIC CARBON COATING APPARATUS HAVING FEED GAS ACTUATOR, filed May 20, 1999; the disclosure of which is incorporated herein by reference.

BACKGROUND OF THE INVENTION

Pyrolytic carbon used to coat parts of heart valve prostheses is formed as a coating on substrates in high temperature deposition processes. A fluidized bed reactor is generally used for the coating operation. In the deposition process a gas stream, consisting of a mixture of hydrocarbon gas (e. g. propane, acetylene, methane, propylene or the like) and an inert gas (e. g. helium, argon, nitrogen or the like), is metered through a vertical heated graphite chamber containing a bed of spherical particles or beads. The shape of the graphite reactor chamber at the gas entrance is generally conical. The gas stream fluidizes or levitates the bed of particles along with valve component substrates suspended within the bed and a part thereof. Pyrolytic carbon coating apparatii of this kind are disclosed in U.S. Pat. Nos. 5,262,104; 5,305,554; 5,332,337; 5,328,720; 5,284,676; 5,328,713; 5,514,410; 3,676,179; 3,677,795 and 3,977,896, each of which is incorporated herein by reference.

The pyrolytic carbon used in heart valves is a form of high density, high wear resistant, high strength carbon. From the biomedical point of view it is noteworthy because of its biocompatibility. From scientist's perspective it is a high technology material which is prepared as a coating on substrates in a fluidized bed and elevated temperature deposition process. In the deposition process a suitable hydrocarbon gas (e. g. propane) along with neutral gas (e. g. helium, argon and/or nitrogen) is metered through a vertical heated graphite chamber containing a bed of granular particles. The shape of the graphite chamber at the entrance is generally conical. This gas stream fluidizes, i. e. levitates and agitates the bed of particles along with any valve substrate components suspended in the bed. The fluidized bed is generally heated in one manner or another, preferably by furnace. The heated bed, in turn, heats the gases. When sufficiently hot, the reactant gases, such as propane and/or other hydrocarbon gases, pyrolyze, thereby dehydrogenating, and form pyrolytic carbon as a solid coating. The pyrolytic carbon coating deposits on the suspended valve components as well as the bed of granular particles. The action of the fluidized bed causes the valve components to continuously circulate through out the bed resulting in coating over their entire surface.

According to the disclosure provided in U.S. Pat. No. 3,977,896 to Bokros et al. (Bokros '896 patent), one of the key parameters which determine the structure of pyrolytic carbon, is the ratio of available deposition surface area relative to the volume of hot zone occupied by the fluidized bed of particles. In the '896 patent disclosure, this parameter is used as a variable for characterizing carbon coating processes. It is believed by the present inventor, that pyrolytic carbon deposited on levitated valve components has certain desirable properties when the surface area of the particles is fairly high when compared to the surface area of the valve components. When such sub-millimeter particles are being coated along with valve components in a fluidized bed, the total surface area of the particles begins to increase significantly as the diameters of the particles increase. However, because of the substantial growth of surface area of the particles, most of the carbon deposition is deposited on the particles rather on the valve components. The coating thickness thus obtained on the valve components is fairly limited. The coating thickness required for manufacture of heart valves is generally higher than possible via the process described above. In order to overcome this difficulty, researchers developed a technique in which small size particles were fed to the hot zone and large coated particles were removed from the coating chamber during the deposition process without causing undue disruption to the process. The Bokros '896 patent is probably the first patent that disclosed the concept of feeding the small size beads and withdrawing the larger coated beads during the deposition process. This technique made it possible to achieve thicker coatings required for heart valve applications.

The Bokros '896 patent describes a number of process parameters for carrying out coating processes. A detail review of specific items pertinent to the fluidized coating reactor apparatus and the process parameters disclosed therein is provided below.

Particle Feed and Purge Systems

As mentioned above, the Bokros '896 patent discloses an apparatus for carrying out coating processes. The patent mentions process parameters for depositing coatings having desirable properties, and feed and withdrawal systems for achieving relatively thick (at least 150 micrometers or microns) coatings. Coating thicknesses greater than 150 microns are believed to be possible by lengthening the duration of coating period. The Bokros '896 patent discloses the idea, the apparatus, and a method of feed and withdrawal of particles. The particle withdrawal is carried out by utilizing a small diameter tube that is placed alongside a wall within the deposition chamber. A neutral gas is continually passed upward through this tube. By adjusting the upward flow rate of neutral gas, coated particles of varying quantities are removed from the fluidized bed. The height of the tube is less than 5 cm above the conical section of the chamber. The internal diameter of the withdrawal tube is such that a helium gas flow of 4 liters per minute prevents removal any particles from the fluidized bed. The withdrawn particles are volumetrically metered. By adjusting the upward flow rate of neutral gas through the withdrawal tube, a purge rate at 90 to 150 cubic centimeters per hour can be achieved. The feed particles are fed via a similar size tube placed along the cylindrical wall of the chamber. The particles are fed intermittently or continuously near the fluidized zone from the top. The feed tube is continually purged with sufficient downward flow of neutral gas.

Source Materials

The Bokros '896 patent discloses several hydrocarbon gases such as methane, propane, ethane, butane, acetylene and propylene for depositing pyrolytic carbon coating. Helium, argon and nitrogen gas are used as neutral gases. The examples given describe use of propane and helium gases for depositing pure and silicone alloyed pyrolytic carbons.

In each of these systems, the pyrolytic carbon comes from the propane or other hydrocarbon gas which enters the reactor and is deposited on the valve component substrates by an endothermic chemical decomposition reaction described for example, in the systems employing propane, by the reaction provided immediately below:

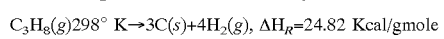

$C_3H_8(g) 298° K \rightarrow 3C(s) + 4H_2(g)$, $\Delta H_R = 24.82$ Kcal/gmole

The reactor chamber is heated by an electrical heating element which in turn heats the gases. When the gases are sufficiently hot, the hydrocarbon gas breaks up or decomposes by a process called pyrolysis to form a pyrolytic carbon coating on the beads and on the valve component substrates, and gaseous hydrogen. The helium or other inert gas serves as an inert carrier/fluidizing gas. The inert, or neutral, gas does not react in the decomposition reaction. The pyrolytic carbon coating is deposited on the suspended valve component substrates, as well as on the beads, under suitable conditions. The action of the fluidized bed generally causes the valve components to circulate through the entire bed, resulting in coating over all exposed surfaces.

In the reactors presently used to coat components of heart valves, the gas stream from the gas inlet into the reactor is believed to be a steady stream of gas. The stream of gas may be metered, but it will still be a steady stream having a constant flow. At times, such a system will malfunction when two or more of component parts become engaged with one another against the inner wall of the reactor, thereby disrupting the bed by immobilizing a portion of it, and thereby changing the coating parameters of the "run" such that a consistent coating process cannot be maintained.

Furthermore, in order to obtain consistent coating on valve components or the like coated in consecutive or non-consecutive batch operations, strict attention must be paid to keeping all parameters exactly the same. This is a difficult task at best. Indeed, it is believed that consistent coating in pyrolytic coating processes cannot be obtained without at least some variance from batch to batch with the prior art coating apparatus described in the Bokros '896 patent, or those generally used at present for batch process coating processes. This is because each reactor has its own irregular frequencies which change with the time of the run as the suspended substrates and beads are coated. New uncoated beads are metered into the bed and coated beads are removed from the bed in order to maintain a generally consistent average weight and density for the beads, but the weight and density of the substrates increase throughout the run. This results in alterations in fluidized bed action within the reactor, and leads to undesirable inconsistencies in the coating deposited on the various substrates during the run.

Accordingly, it will be appreciated that there is a need for an efficient pyrolytic carbon coating apparatus or system for providing a consistent coating of pyrolytic carbon on valve components and the like. The present invention provides advantages over the prior devices and prior methods used to coat valve components, and also offers other advantages over the prior art and solves other problems associated therewith.

SUMMARY OF THE INVENTION

The pyrolytic carbon coating apparatus of the present intention includes a fluidized bed reactor having a reactor chamber, a gas feed inlet, and an exhaust gas outlet, a source of process feed gas, preferably including a mixture of gaseous hydrocarbons and inert carrier gases, more preferably including gases selected from the group consisting of gaseous hydrocarbons, inert carrier gases and mixtures thereof, and a gas line through which the process feed gas can pass from the source of process feed gas to the gas feed inlet and into the reactor chamber. The fluidized bed reactor is of a type which generally permits the levitation or fluidization of substrates in a pyrolytic carbon coating environment where gaseous hydrocarbons within the process feed gas is decomposed at elevated temperatures in order to coat surfaces of fluidized substrates with pyrolytic carbon. The gas line of the present invention includes an actuator which varies the rate of flow of process feed gas into the reactor chamber, such that the flow of process feed gas, through the gas line to the reactor chamber when the reactor chamber is occupied by a fluidized bed including at least one or preferably plurality of substrates to be coated by pyrolytic carbon, cycles regularly over a consistent period of time from a higher flow rate to a lower flow rate and vice versa, so as to create a pulsating gas flow and a pulsation effect upon the fluidized bed within the reactor chamber. The preferred actuator includes a bypass line and a main line through which process gas can flow. The bypass line includes a metering valve, preferably a needle valve, which can be used to restrict the flow of process gas through the bypass line. The main line includes a gas filter, preferably a high purity gas filter, through which the process gas flows prior to flowing through a switch valve, preferably an oscillating solenoid valve, which opens and closes in a regular cycle thereby alternately stopping and permitting the flow of process gas through the main line. The bypass line and the main line both diverge from and subsequently rejoin the gas line to direct a pulsating flow of process feed gas through the gas line into the reactor chamber having a flow rate which regularly cycles from a higher flow rate to a lower flow rate and vice versa. The apparatus enhances the ability of the user to provide a consistent coating of pyrolytic carbon on different sizes and types of component substrates. This is particularly desirable for individual components of heart valve prostheses.

The present pyrolytic carbon coating apparatus allows one to control the frequency and amplitude of the pulsating feed gas flow rate. As the needle valve in the bypass line is moved toward a closed position, thereby decreasing the rate of flow through the bypass line, the difference between the higher flow rate and the lower flow rate increases. As the needle valve in the bypass line is opened, thereby increasing the rate of flow through the bypass line, the difference between the higher flow rate and the lower flow rate decreases. The frequency and the amplitude can be controlled in a manner which allows this use to produce coated component parts having consistent coating parameters from one batch to another. A sufficient flow of steady process gas through the bypass line is maintained so as to avoid the collapse of the fluidized bed.

It is an object of the present invention to provide a reactor in which gaseous hydrocarbons are efficiently decomposed to form a pyrolytic coating on substrate surfaces which is of greater quality than that which has been previously available, and which can be applied to the substrate surfaces more evenly and consistently over a series of batch coating processes, while creating less soot buildup within the reactor chamber.

These and various other advantages and features of novelty that characterize the present invention are pointed out with particularity in the claims annexed hereto and forming a further part hereof. However, for a better understanding of the present invention, its advantages and other objects obtained by its use, reference should be made to the drawings, which form a further part hereof and to the accompanying descriptive matter, in which there is illustrated and described preferred embodiments of the present invention.

BRIEF DESCRIPTION OF THE DRAWINGS

The invention will be further described in connection with the accompanying drawings, in which.

DETAILED DESCRIPTION OF THE PREFERRED EMBODIMENTS

Figure 1:
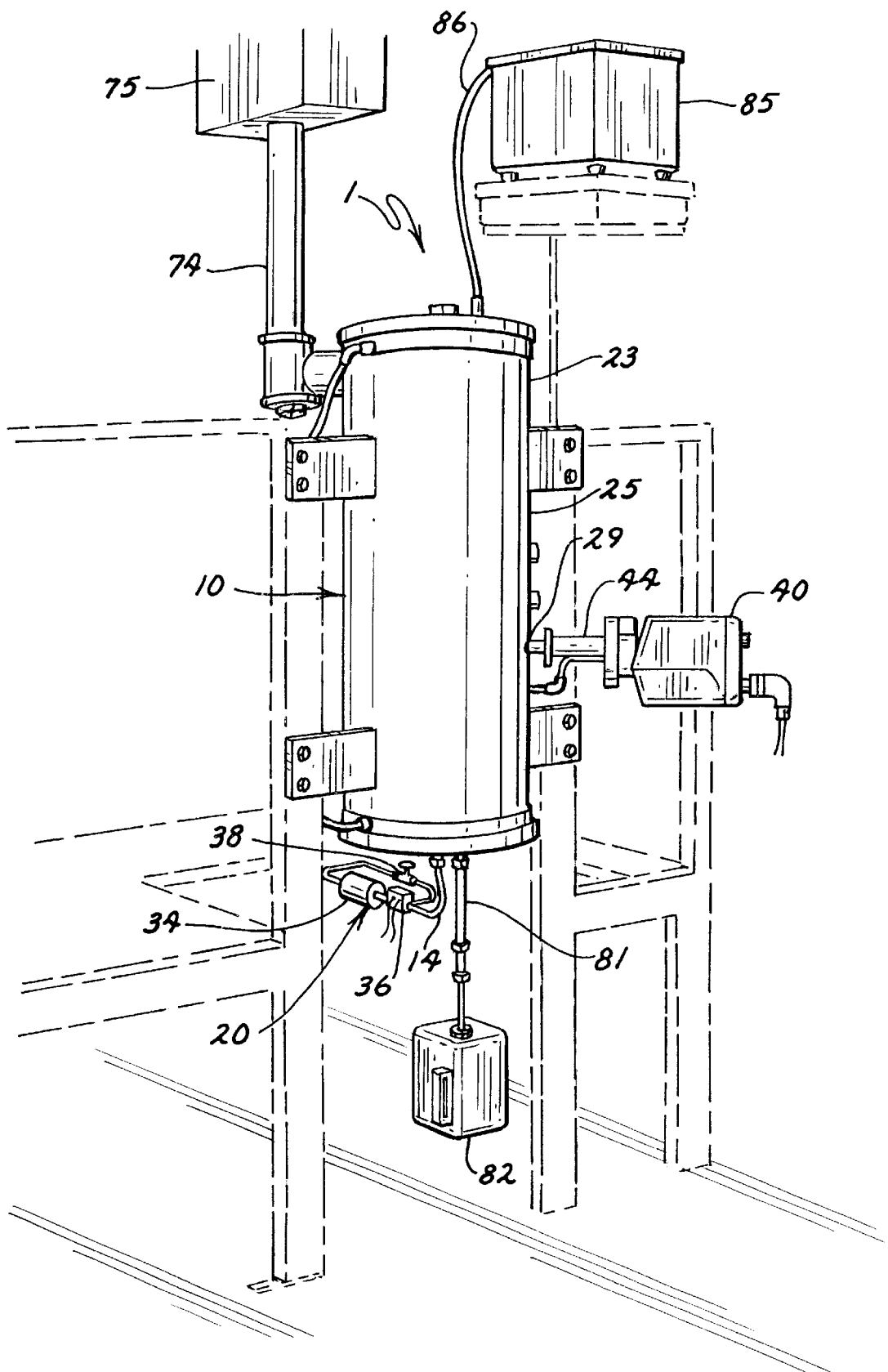
FIG. 1 is a perspective view of the pyrolytic carbon coating apparatus of the present invention in its environment.
Figure 2:
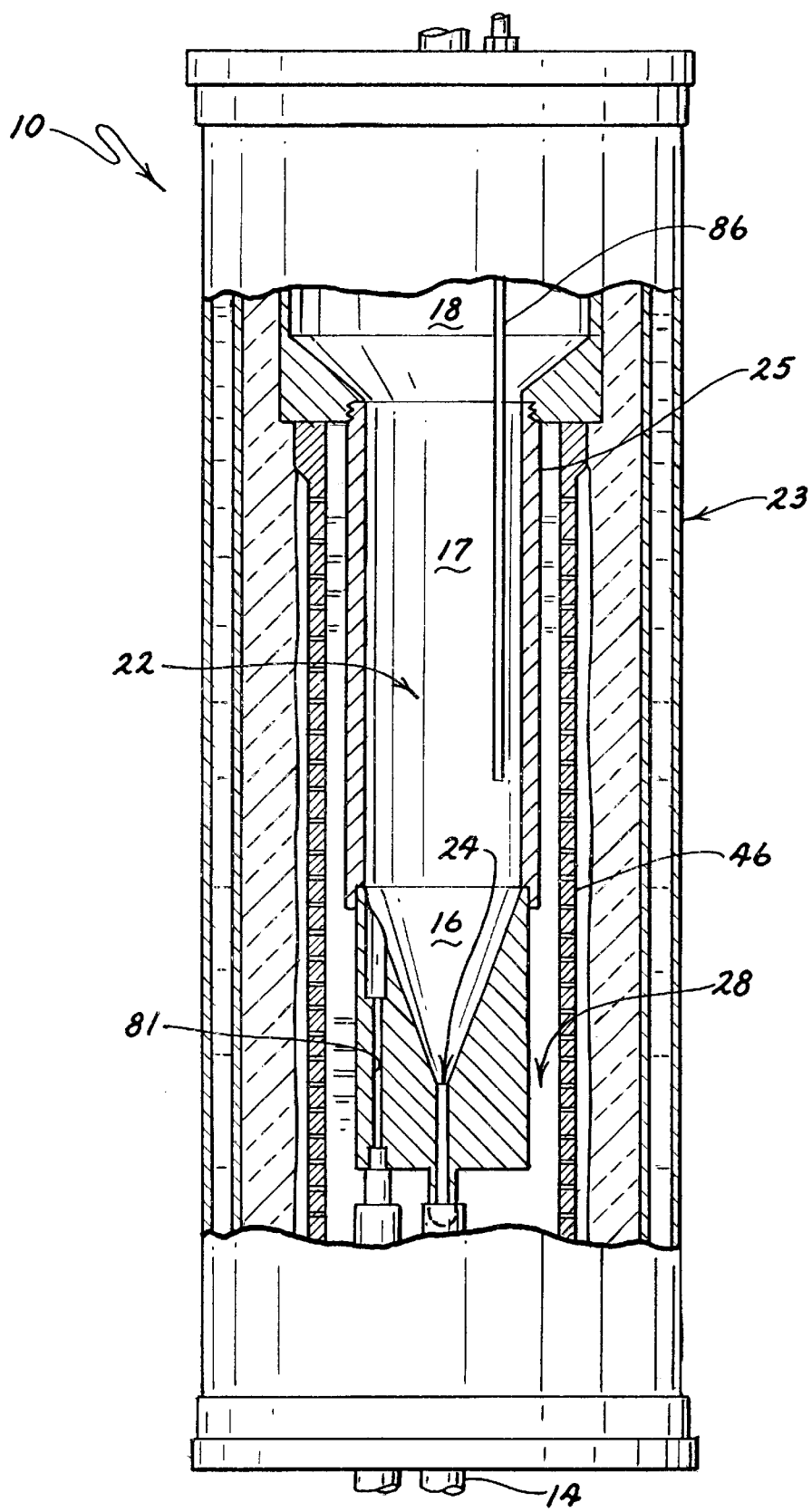
FIG. 2 is a side view of the reactor shown in FIG. 1, but showing the reactor partially broken away to show a portion of the reactor in cross-section.

Referring now to the Figures, a preferred pyrolytic carbon coating apparatus 1 is shown. In FIGS. 1 and 2 parts of the apparatus 1 are shown and in FIG. 3 a schematic drawing of a preferred apparatus 1 is provided. The preferred pyrolytic carbon coating apparatus 1 includes a reactor 10, a source of process feed gas and inert purge gas 12, preferably including a mixture of gaseous hydrocarbons and inert carrier gases, more preferably including gases selected from the group consisting of gaseous hydrocarbons, inert carrier gases and mixtures thereof, any of which can be supplied separately, a gas line 14 and an actuator 20. Process gas, preferably gaseous hydrocarbons mixed with inert carrier gases, may pass from the source of process feed gas 12 to a reactor chamber 22 via the gas line 14. The gas line 14 communicates with the reactor chamber 22 via a gas feed inlet 24 and gas passes out of the reactor chamber 22 via an exhaust gas outlet 26. The process gas flows from the source of process feed gas 12 to the gas feed inlet 24 via the gas line 14, passing through the actuator 20. The actuator 20 includes a bypass line 30 and a main line 32. The main line 32 preferably passes through a high purity gas filter 34 and an oscillating solenoid 36 in series which are bypassed by the bypass line 30. Gas flowing through the bypass line 30, however, can be metered using a needle valve 38 through which the bypass line 30 flows. During operation of the reactor 10, the flow of process gas through the bypass line 30 is restricted using the needle valve 38 and flow through the main line 32 is cycled by regularly opening and closing the oscillating solenoid valve 36 to create a pulsating gas flow and a pulsation effect upon the fluidized bed (not shown), within the reactor chamber 22.

The preferred reactor 10 has a water cooled shell 23 which is shown in FIGS. 1 and 2. The reactor temperature is measured by using an optical pyrometer 40 to make an optical pyrometer sighting at a spot 29 on the outer side wall 25 of the reactor chamber 22 via a sight port 44. The temperature is controlled by regulating electrical power input to a graphite heating element 46 surrounding the reactor chamber 22. The heating element 46 is interconnected with an electrical power source (not shown) by a pair of electrodes (not shown). The heating element 46 and the reactor chamber 22 are enclosed within the water-cooled stainless steel shell 23. The water-cooled gas feed inlet or injector 24, the water-cooled bead receiving conduit or injector 81 and each of the electrodes (not shown) which heat the heating element 46 are cooled by cold water circulating through the shell 23. The water is preferably supplied from a well or other water source. In alternate embodiments (not shown), the water can be pumped through the water conduit by a pump driven by a power source, and the water can be cooled by a cooling unit.

The air space 28 between the reactor chamber 22 and the shell 23 is partially filled with insulation (not shown) and otherwise occupied by purge gas, preferably nitrogen, from a first purge line 27 which communicates with the air space 28 and a source of inert gas (not shown) within the source of process gas and inert gas 12. The fluidization or feed gases are introduced into the hot zone of the reactor chamber 22 via a water-cooled injector 24 or injectors which preferably communicate with the water cooling space 29 of the water cooled shell 23. These water cooled injectors 24 prevent the gases from overheating prior to entering the reaction zone, thus avoiding premature pyrolysis and deposition. Injectors 24 and graphite reactor chamber 22 are supported and sealed by springs (not shown). The springs also allow for the expansion and contraction of the reactor chamber 22 during heating and cooling. All gases (i.e. helium (He), nitrogen ($N_2$), and propane ($C_3H_8$)) are kept at specified pressures by pressure regulators (not shown). The gases are preferably passed through individual solenoid valve switches (not shown) and then through mass flow controllers (not shown) and then through mass flow controllers within the source 12 of feed gas and inert purge gas. Next gases preferably go through reactor selector solenoid valve switches (not shown) and then to the reactor 22. All pressure regulators, solenoid valves and mass flow controllers are preferably enclosed in a valve cabinet (not shown). Separate cabinets are preferably provided for power supplies. The incoming cooling water for the reactor 10 preferably goes through a solenoid valve (not shown) and then water line 62 is split into a number of separate streams to cool the gas injectors, a top flange (not shown) the electrodes (not shown) and of the shell 23. The water lines preferably have temperature indicators (not shown) and flow meters (not shown) for easy visual indication. A nitrogen supply line (not shown), within the source 12 of feed gas and inert purge gas, provides inert gas for the process, shell purge, sight port purge, reactor/process purge, bead removal purge and the ballast. The sight port purge stream is further split for purging the pyrometer sight port 44, bead feeder assembly 85 and, in preferred embodiments (not shown) a top sight port (not shown) is provided. The total flow in these purge lines is controlled by mass flow controllers (not shown) and individual lines are preferably monitored by flow meters (not shown). The main helium supply line (not shown) is preferably split into a total of two streams (not shown). The first stream (not shown) is used for process gas. The second stream (not shown) is sent to the bead catch pot 82 for controlling bead removal during the run. An optical pyrometer 40 is set to read the temperature at a fixed spot 29 on the outside wall of the reactor 10. Based on this signal, input to the power supplies is adjusted for heating the reactor chamber 22 to the desired set point.

The reactor chamber 22 of the preferred carbon coating apparatus 1 has a conical lower region 16, which is typical of conical inlet fluidized bed reactors, a cylindrical middle region 17 and an upper cylindrical region 18 having a larger inside diameter than the middle region. The inside diameter "A" of the cylindrical middle region is about 8.9 cm, and the volume of the reactor chamber 22 is approximately about 835 cc. In alternate embodiments (not shown), the inside diameter will be in a range of from about 7.5 to about 13 cm, however, reactor chambers of any practical size are envisioned within the scope of the present invention.

The present apparatus 1 also includes a bead catch pot 82 and a bead receiving conduit 81 which are in communication with a source of inert purge gas. The purge gas (not shown), preferably helium, flows into the reactor chamber 22 from the bead catch pot 82 and the bead receiving conduit 81. The present apparatus 1 also includes a bead feed receptacle 85 and a bead feed conduit 86 in communication with the reactor chamber 22 for feeding uncoated beads (not shown) into the reactor chamber 22 from the bead feed receptacle 85 via the bead feed conduit 86. The bead feed conduit 86 is in communication with both the reactor chamber 22 and the bead feed receptacle 85, and the bead feed receptacle 85 and a bead feed conduit 86 are in communication with a source of inert purge gas (not shown) within the source 12 of feed gas and inert purge gas. The purge gas (not shown), preferably nitrogen, flows into the reactor chamber 22 from the bead feed receptacle 85 and the bead feed conduit 86. The bead feed receptacle 85 preferably includes an auger (not shown) which is preferably powered by a power supply (not shown). The purge gas is supplied and the beads are fed and removed generally in the same general manner as described in the Bokros '896 patent, referenced hereinabove, which is incorporated herein by reference. Care is generally taken to assure that the rate of flow of the purge gas to the catch pot 82 is such that only a desired number of beads fall into the catch pot 82 via the bead receiving conduit 81, so that the bed size may be maintained at a desirable size which permits efficient coating of substrate surfaces. Other aspect of the operation of the preferred apparatus such as the cooling and other aspect are managed in much the same way as such operations are managed for most of the key prior art methods in the pyrolytic carbon coating industry.

Coating Operation:

In coating process the stream of feed gas, preferably consisting of a mixture propane and helium is sent through the central process injector or gas feed inlet 24 into the heated graphite chamber containing a bed of spherical particles (not shown). The gas stream fluidizes the bed of particles along with valve substrates (not shown) suspended in the bed. When sufficiently hot, propane and other gaseous hydrocarbon molecules break up by process known as pyrolysis to form pyrolytic carbon as coating. The helium serves as an inert carrier fluidizing gas. The action of the fluidized bed causes the valve components to circulate through the entire bed resulting in coating over all exposed surfaces. During coating operations, ceramic beads, preferably zirconium oxide beads, are fed continuously into the hot zone of the reactor at a preset rate and coated beads are removed from the fluidized bed via a purge tube. The weight of the purged beads may be monitored continuously using a scale (not shown). The bead feed tube and feed assembly are purged with an inert gas throughout the coating run. The removed beads are collected in the catch pot 82. The rate of bead removal is controlled by the upward flow of helium gas through the purge tube 81. The space between the graphite reactor and the shell, the bead feed system and the bead removal box is purged with an inert gas. Accurate measurement and control of temperature, helium flow, propane flow, bead feed and bead removal is preferably maintained throughout the run. These measurements are taken and displayed on a PC monitor to indicate the current run status to the operator. During coating, uncoated beads of about 350 to about 500 micrometers in diameter are introduced into the reaction zone of the reactor chamber 22 and coated beads of over about 600 micrometers in diameters are removed. The coated beads generally have a lower density than the uncoated beads due to the lower density of the pyrolytic carbon coating. Along with that the valve components get heavier due to carbon deposition. All these factors are continually influencing the dynamics or the activity of the bed. Under these circumstances even with ideal control of gas flow rates, bead sizes, bead feed and removal operations the circulation of the components is governed by the unpredictable random mixing caused by the fluidizing gases. In some instances due to unpredictable nature of random mixing some components could clump together which may result in total collapse or freeze-up of the bed. In this mode of operation there is no consistency to circulatory mixing action from one run to the next. Also the circulatory mixing action is expected to be different for various sizes, types, and loads of components chosen. Hence a method that ensures consistent circulatory mixing of valve components during coating run as well as between runs is vitally essential for depositing high quality coating material on various sizes, types, and component loads.

To satisfy this need, an innovative device called actuator 20 has been developed. The actuator 20 provides consistency between runs and also ensures deposition of high quality material by controlling the bed activity during coating runs for various sizes, types, and loads. The actuator 20 imparts pressure perturbations of predetermined frequency and amplitude to the fluidized bed via the process gas line 14. These perturbations maintain consistent circulatory action of valve components during coating and diminish the likelihood of bed freeze-ups. An improved mixing action means better heat and mass transport which leads to overall enhancement in the efficiency of the process. A pressure transducer and amplifier 54, in combination with an oscilloscope 56, a pressure gauge 57 and a differential pressure gauge 59, enable the operator to monitor the mean upstream pressure, its amplitude, its frequency and the differential pressure, so that the bed action can be maintained at optimum levels by a combination of managing bead feed and removal, and settings of flow rates and timing of the actuator 20. Thus the bed size and the circulation of the valve components can be controlled for improved coating efficiency. In alternate embodiments (not shown) all data is monitored and all inputs are controlled using computer control systems which are well known in the art. A detailed description of the preferred actuator 20 is provided hereinbelow.

Figure 3:
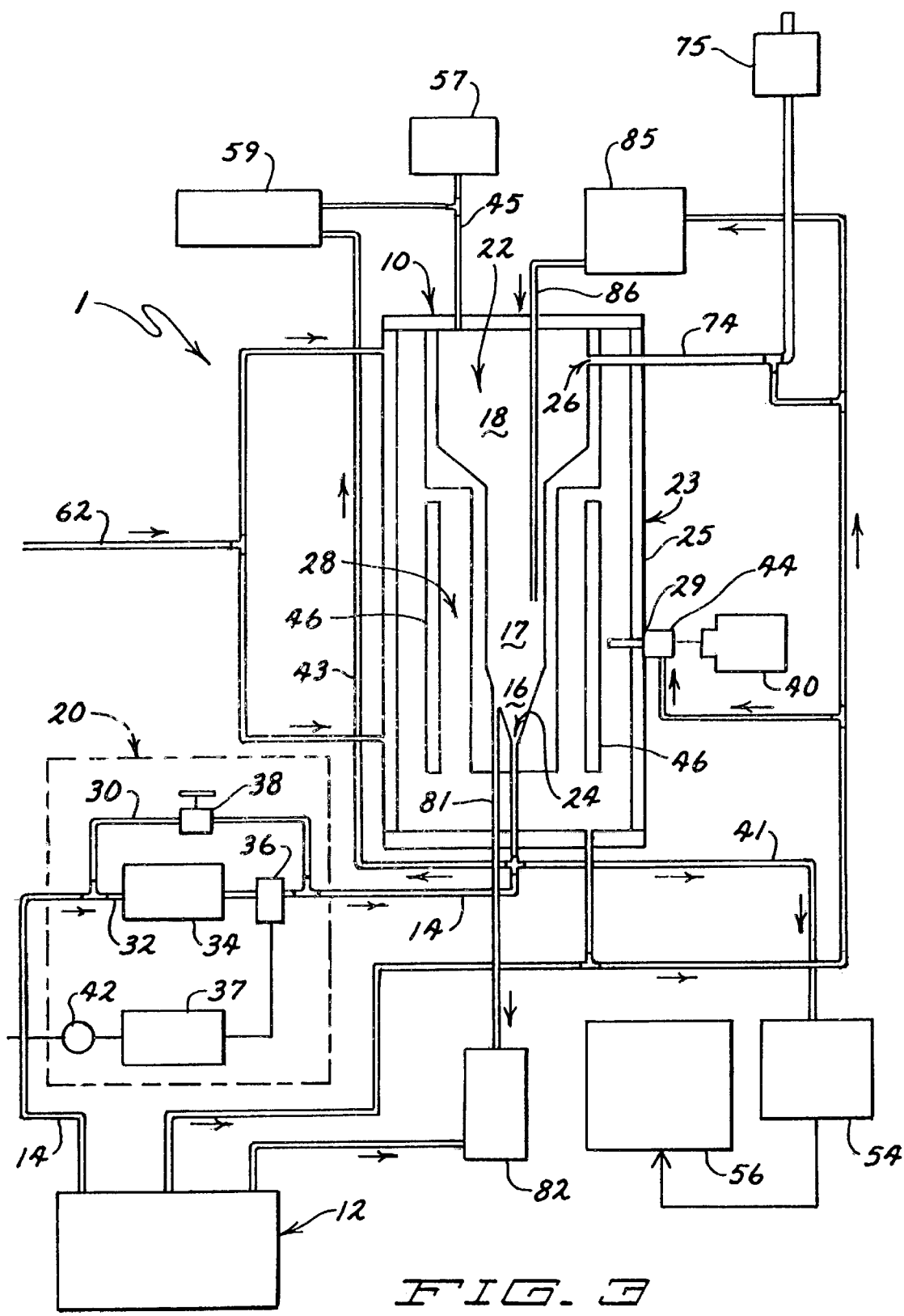
FIG. 3 is a schematic representation of the preferred pyrolytic carbon coating apparatus of the present invention, showing the reactor in partial cross-section.

Actuator Set-Up:

The components that constitute the actuator 20 are shown within the dotted line box in FIG. 3. As seen in the schematic the process gas line 14 diverges into a bypass loop or line 30 and a main line 32. The main line 32 includes a high purity filter 34 and an oscillating solenoid valve 36. A combination power supply 42 and timing circuit 37 are connected in series to the oscillating solenoid valve 36 to provide power and timing for the opening and closing of the valve 36. The bypass line 30 includes a stainless steel needle valve 38 to regulate the gas flow through the line 30. A couple of pressure sensing lines 41,43 are preferably connected at upstream of the process gas injector. The pressure transducer 54 is preferably connected to the first line 41. A signal from this transducer is amplified and then monitored on an oscilloscope 56. The other pressure sensing line 43 along with and an additional pressure sensing line 45 from the top of the reactor communicate with a differential pressure gauge 59. This gauge 59 monitors the pressure difference between the upstream of process gas injector 24 and the top of the reactor. The gas lines are preferably 0.375 inch stainless steel tubes. The following instruments are used in a typical set-up: 1) Gas filter: All Welded High Purity Line Filter, Model No. 6134T6FF, from Matheson Gas Products, Montgomeryville, Pa. 18936.2) Needle valve: Whitey, Minnesota Valve & Fittings Co., Eden Prairie, Minn. 3) Differential pressure gauge: Photohelic Series 3000 SGT Pressure Switch/Gage/Transmitter, 0 to 10 mm Hg, Dwyer Instrument, Inc., Michigan City, Ind. 46360.4) Solenoid valve: Model no. 111B-591CAA, 24 VDC, 2.5 Watts, vacuum to 150 psi, Mac Valves, Inc., Wixom, Mich. 48393.5) Timing circuit: 555 Timer IC Circuit (Basic Astable Circuit), Radio-Shack, Fort Worth, Tex. 76102.6) Signal amplifier: Model CD 19, Carrier Demodulator, Validyne Engineering, Corp., Northridge, Calif., 91324.7) Digital oscilloscope: Model 5110, Tektronix, Beaverton, Oreg., 97077.8) Pressure transducer: Deltran I, Model 6069, −50 to 300 mm Hg, Utah Medical Products, Inc., Midvale, Utah, 84047.9) Power supply: 110 Volts AC to 24 Volts DC, 26.4 Watts, P/N 123271, Jameco Electronic Components, Belmont, Calif. 94002.

The timer frequency and the needle valve position are adjusted while monitoring the pressure signal on the oscilloscope. Generally, the pressure amplitude is in a range of about 2 to about 100 mm Hg, preferably about 4 to about 40 mm Hg, most preferably about 5 to about 20 mm Hg. The frequency can range from about 2 to about 15 Hz, preferably from about 5.5 to about 7.5 Hz. The coating is preferably started by gradually increasing the propane flow to a required level and simultaneously decreasing the nitrogen flow through the central process injector 24 to zero. The upstream reactor pressure and its frequency are monitored continuously on the gauges and the oscilloscope respectively. The perturbations generated by the oscillating solenoid valve are passed through the central process injector into the reaction chamber. There the perturbations help maintain consistent circulatory action of valve components during coating and diminish the likelihood of bed freeze-ups during coating run. With the actuator 20, the mean upstream pressure, its amplitude and its frequency are maintained at optimum levels by combination of bead feed and removal, and optimized settings of the actuator. Accurate measurement and control of temperature, helium flow, propane flow, bead feed and bead removal is maintained throughout the run. In alternate embodiments, all of these measurements are taken and displayed on a PC monitor (not shown) to indicate the current run status to the operator, as well as being recorded digitally so that a record of each run can be retained. Thus, the coating operation may be run under computer control within desired parameters.

In further embodiments, the zirconium oxide particles used in preferred processes employing the present apparatus 1 have diameters from 350 to 600 microns. The particles size range of 425 to 600 microns is typically used for feeding the particles to the bed. The particle removal tube 81 is above the top of the conical surface. The inside diameter of this tube 81 is 0.25 inch. It is believed that because of the fluidizing action, the bed pressure fluctuates with certain periodicity. The pressure amplitude (difference between peaks and valleys) and its frequency are also measured by pressure sensor. It is believed that the measurements of upstream bed pressure, pressure amplitude and its frequency as a group, are better indicators of the fluidized bed activity (i. e., the circulation of valve components within the bed). A consistent circulation of valve components is essential for depositing coating with uniform properties. This is an important factor that is not disclosed in the prior patents. The actuator 10 of the present invention has been developed to impart pressure fluctuations of varying frequency and amplitude to the fluidized bed. In this system, optimum values for the frequency and amplitude can be determined and maintained in order to optimize coating efficiency and the quality of the pyrolytic carbon coating obtained. The carbon deposition process is started with the actuator set at predetermined optimal condition. The upstream pressure, bed pressure amplitude, and frequency are continually monitored. During coating operation the coated particles are removed by varying the upward flow of neutral gas through the particle removal tube to maintain the upstream pressure within a predetermined range. The circulation of valve components is maintained at the required level by adjusting the amplitude and frequency settings of the actuator. Therefore, with this novel and unique method, both bed size and part circulation are controlled which results in uniform quality coating. The preferred process employed with the present apparatus 1 uses propane as the hydrocarbon gas and helium as neutral gas. For fluidizing, zirconium oxide beads having diameters of from 300 to 600 micron are preferred. The reactor chamber 22 or bed chamber is preferably resistively heated.

It is to be understood, however that even though numerous characteristic and advantages of the present invention have been set forth in the foregoing description, together with details of the structure and function of present invention, the sequence or order of the specific steps, or the actual compositions or materials used may vary somewhat. Furthermore, it will be appreciated that this disclosure is illustrative only and that changes may be made in detail, especially in matter shape, size, arrangement of parts or sequence or elements of aspects of the invention within the principles of the invention to the full extent indicated by the broad general meaning of the terms in which the appended claims, which form a further part hereof, are expressed.

What is claimed is:

1. A fluidized bed pyrolytic carbon coating apparatus for coating substrate surfaces of at least one substrate with pyrolytic carbon formed by decomposing gaseous hydrocarbons at elevated temperatures, sufficient to pyrolyze such hydrocarbons, within a fluidized bed within the coating apparatus, the pyrolytic carbon coating apparatus comprising:

a fluidized bed reactor having a reactor chamber, a gas feed inlet and an exhaust gas outlet, the gas feed inlet and the exhaust gas outlet communicating with the reactor chamber;

a source of process feed gas, the feed gas including gases selected from the group consisting of gaseous hydrocarbons, inert carrier gases and mixtures thereof; and a gas line through which the process feed gas passes during transfer from the source of process feed gas to the gas feed inlet, and into the reactor chamber; wherein the gas line includes an actuator including a timing circuit which acts to vary a rate of flow of process feed gas through the gas line into the reactor chamber such that the rate of flow of process feed gas into the reactor chamber, when the chamber is occupied by the fluidized bed including at least one substrate to be coated by pyrolytic carbon, cycles regularly and consistently over a period of time from a predetermined higher flow rate to a predetermined lower flow rate and vice versa, so as to create a pulsation effect upon the fluidized bed within the reactor chamber; the actuator including two separate gas conduits converging from and then rejoining the gas line, namely, a main line and a bypass line, through which the process feed gas can flow; the bypass line including a metering valve that can vary the rate of flow through the bypass line, the main line including a switch valve that can alternately close and open the main line, thereby alternately stopping and permitting flow of process feed gas through the main line.

2. The pyrolytic carbon coating apparatus of claim 1, the reactor including a heating element.

3. The pyrolytic carbon coating apparatus of claim 1, the switch valve being an oscillating solenoid valve.

4. The pyrolytic carbon coating apparatus of claim 1, the main line further including a gas filter in series with the switch valve such that process feed gas flowing from the source of process feed gas passes through the gas filter prior to flowing through the switch valve when the switch valve is open.

5. The pyrolytic carbon coating apparatus of claim 1, further including a pressure sensing device for measuring pressure in the feed gas line.

6. The pyrolytic carbon coating apparatus of claim 5, wherein the pressure sensing device is a differential gauge which measures the pressure in the feed gas line and measures the pressure at the top of the reactor chamber and provides a differential pressure reading between the respective pressure measurements.

7. The pyrolytic carbon coating apparatus of claim 1, further including a bead feed receptacle and a bead feed conduit in communication with the reactor chamber for feeding uncoated beads into the reactor chamber from the bead feed receptacle via the bead feed conduit, the bead feed conduit being in communication with both the reactor chamber and the bead feed receptacle, the bead feed receptacle and a bead feed conduit being in communication with a source of inert purge gas which flows into the reactor chamber from the bead feed receptacle and the bead feed conduit.

8. The pyrolytic carbon coating apparatus of claim 1, further including a bead catch pot and a bead receiving conduit in communication with the reactor chamber for receiving beads from the reactor chamber, the bead receiving conduit being in communication with both the reactor chamber and the bead catch pot, the bead catch pot and a bead receiving conduit being in communication with a source of inert purge gas which flows into the reactor chamber from the bead catch pot and the bead receiving conduit.

* * * * *